United States Patent [19]
Roman

[11] 4,041,027
[45] Aug. 9, 1977

[54] INSECTICIDAL OXIME DERIVATIVES

[75] Inventor: Steven A. Roman, Oakdale, Calif.

[73] Assignee: Shell Oil Company, Houston, Tex.

[21] Appl. No.: 716,918

[22] Filed: Aug. 23, 1976

[51] Int. Cl.$^2$ .......................................... C07D 279/06
[52] U.S. Cl. ..................................... 542/400; 424/246
[58] Field of Search .......... 260/240 G, 240 A, 243 R; 424/246

[56] References Cited

U.S. PATENT DOCUMENTS

| | | | |
|---|---|---|---|
| 3,962,225 | 6/1976 | Powell | 260/243 R |
| 3,962,233 | 6/1976 | Roman | 260/243 R |
| 3,962,234 | 6/1976 | Roman | 260/243 R |
| 3,993,648 | 11/1976 | Powell | 260/243 R |

Primary Examiner—Arthur P. Demers

[57] ABSTRACT

Insecticidal O-substituted derivatives of 5,6-dihydro-4H-1,3-thiazine-2-carboxaldehyde oxime.

1 Claim, No Drawings

INSECTICIDAL OXIME DERIVATIVES

DESCRIPTION OF THE INVENTION

It has been found that useful insecticidal activity is possessed by O-substituted derivatives of 5,6-dihydro-4H-1,3-thiazine-2-carboxaldehyde oxime, these derivatives having the formula:

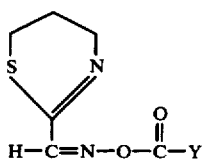 (I)

wherein Y is alkyl or alkoxy of from 1 to 20 carbon atoms; alkenyl, alkenyloxy or alkynyl of from 3 to 20 carbon atoms; cycloalkyl, alkylcycloalkyl or cycloalkylalkyl of from 3 to 10 carbon atoms, with from 3 to 6 carbon atoms in the ring; alkoxycarbonylalkyl of from 3 to 10 carbon atoms; alkylthioalkyl of from 2 to 10 carbon atoms; di($C_1$-$C_4$ alkoxy)phosphinyloxy($C_2$-$C_6$ alkenyl)-; styryl; mono($C_1$-$C_4$ alkyl or alkoxy)phenyl; phenyl optionally substituted by from 1 di($C_1$-$C_4$ alkyl)amino, nitro, cyano or phenoxy, heteroaryl selected from 2-furanyl, 2-thienyl, 2- and 3-pyridyl, and their corresponding phenylmethyl and heteroarylmethyl counterparts; or is

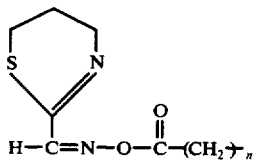

wherein n is 0, 1, 2, 3 or 4.

Any aliphatic moiety in these compounds suitably is of straight-chain or branched-chain configuration.

For illustration, preparation of typical individual species of the genus is described in the examples included hereinafter. Other typical individual species of the genus are those wherein Y is:
2-pyridyl
1-propenyl
benzyloxy
cyclopropylmethyl
cyclohexyl
2-propenyloxy
propargyl
cyclohexylmethyl
ethynyl
furfuryl The compounds of the invention can exist in the form of two geometric isomers, the E- and Z- forms. Because of the relative sizes of the moieties involved, it is probable that the predominant form is the E- form. The invention contemplates both isomers, as well as mixtures thereof.

Compounds of this invention can be prepared by treating 5,6-dihydro-4H-1,3-thiazine-2-carboxaldehyde oxime with a 1-(Y-carbonyl)-3-methylimidazolium chloride by the method described by E. Guibe-Jampel, et al., Bull. Soc. Chim. Fr. 1973 (3) (Pt. 2), pp. 1027–7. According to this method, the imidazolium chloride is prepared by treating 1-methylimidazole with the appropriate acid chloride, Y—C(O)—Cl, or chloroformate, Y—O—C(O)Cl, preferably in a suitable solvent and at a low temperature, for example, about 0°–5° C. A suitable general method for conducting this procedure comprises adding a solution of the acid chloride in methylene chloride slowly (e.g., dropwise) to a cold (e.g., 0°–5° C) solution of the N-methylimidazole in the same solvent, stirring the cold mixture for a period of from about 15 minutes to one hour to ensure essentially complete reaction, then adding to that stirred cold mixture a solution of the oxime, then warming the stirred mixture to a temperature of from about room temperature to the reflux temperature, and stirring the warm mixture for a time to ensure essentially complete reaction.

The desired product can be isolated from the crude reaction mixture and purified by conventional methods, such as filtration, extraction, crystallization and elution (chromatography).

These procedures for preparing compounds of this invention are illustrated in the following examples of the preparation of particular species of such compounds. In all cases, the identity of the product, and of any intermediate employed, was confirmed by appropriate chemical and spectral analyses.

EXAMPLE 1

5,6-dihydro-4H-1,3-thiazine-2-carboxalde O-benzoyloxime (1)

320 g of tetrahydro-2-nitromethylene-2H-1,3-thiazine (U.S. Pat. No. 3,933,809) was dissolved in 2 liters of methylene chloride. To the stirred solution at room temperature 237.4 g of methyl fluorosulfonate was added over a one-hour period. The reaction mixture temperature rose to 36°. The mixture was stirred for one hour, then a solution of 210 g of sodium bicarbonate in 2 liters of water was added over a 30-minute period and the mixture was stirred for an additional 30 minutes. The methylene chloride phase was separated, washed with water, dried (MgSO$_4$) and filtered, and the solvent was evaporated until the volume of the solution was 1150 ml, the solution being kept cold; this solution is 1A.

3.5 liters of toluene was heated to boiling, and while stirring, 1A was added, the heating and rate of addition of 1A being adjusted so that the reflux temperature was in the range of 98°–103° (the addition required 2 hours). During the addition, methylene chloride was allowed to distil off. The mixture then was stirred at 100°–105° for 1 hour. Then 15 g of charcoal was added and the hot mixture was filtered. The filtrate (3.3 liters) was concentrated to 2 liters and allowed to cool slowly, to give 5,6-dihydro-4H-1,3-thiazine-2-carboxaldehyde oxime (1B), m.p.: 141°–144° C.

2.7 g of 1-methylimidazole was dissolved in 100 ml of tetrahydrofuran at 5°. Over at 15-minute period, a solution of 4.6 g of benzoyl chloride in 20 ml of tetrahydrofuran was added thereto. The mixture was stirred for 30 minutes at 5°, then 4.3 g of 1B was added. The mixture was allowed to warm to room temperature and stirred for 30 minutes. Then the solvent was stripped off and the residue was diluted with methylene chloride. Then water was added and the two phases were separated. The solvent phase was dried (MgSO$_4$), filtered and stripped of solvent to give an oil. The oil was crystallized from pentane and the crystals were recrystallized from hexane to give 1, as colorless crystals, m.p.: 114°–115° C.

EXAMPLE 2 - 27

By the general technique described in Example 1, the following further specific compounds of this invention were prepared, being described in terms of moiety, Y, formula I, with the indicated physical properties.

| Example No. | Compound No. | Y | Melting Point, ° C |
|---|---|---|---|
| 2 | 2 | 4-nitrophenyl | 134 (with decomposition) |
| 3 | 3 | 2-(methoxyphosphinyloxy)propenyl | 74 – 74.5 |
| 4 | 4 | methoxy | 81 – 81.5 |
| 5 | 5 | methyl | 52.5 – 53 |
| 6 | 6 | tert-butyl | 29.5 – 30.5 |
| 7 | 7 | 2-(methylthio)ethyl | 69 – 70 |
| 8 | 8 | pentyl | (liquid; boiling point not determined) |
| 9 | 9 | styryl | 143 – 144 |
| 10 | 10 | 2-furanyl | 107.5 – 108 |

Compounds of this invention exhibit useful insecticidal activity, being of particular interest for control of the larvae "caterpillar" of "worm" forms of insects of the genus Heliothis, such as H. *zea* (corn earworm, cotton bollworm, tomato fruitworm), H. *virescens* (tobacco budworm); the genus Agrotis, such as A. *ipsilon* (black cutworm); the genus Trichoplusia, such as T. *ni* (cabbage looper), and the genus Spodoptera, such as S. *littoralis* (Egyptian cotton leafworm). Some are also of interest for controlling aphids and houseflies. In tests that have been conducted they have exhibited low, or no, toxicity to other insects such as the 2-spotted spider mite and mosquito larva. Some act rapidly, providing "quick knock-down" of insects, in some cases even though the compound is not very toxic to the insects.

Activity of compounds of this invention with respect to insects was determined by using standardized tests to establish the $LC_{50}$ dosage (in milligrams of test compound per 100 milliliters of solvent or liquid carrier required in the solution or suspension of test compound used) to kill 50% of the test insects. The test insects were the housefly, corn earworm, pea aphid and 2-spotted spider mite, and in some cases, the black cutworm. Activity with respect to mosquito larvae was determined by placing the larvae in water containing the test compound.

All of compounds 1 through 27 were found to be active with respect to the corn earworm. Compounds 1, 3–9, 11–20, 22, 23 and 25–26 were found to be active with respect to the housefly. Compounds 1, 3–8, 10–11, 15–20, 22, 23, 25 and 26 were found to be active with respect to the pea aphid. Compound 3 was active with respect to the mites. Compounds 2, 8, 9, 11–13, 20, 22, 24 and 25 were slightly active with respect to the mosquito larvae.

In the course of these tests it was noted that compounds 3–7, 14, 17 and 26 acted quickly on houseflies, compounds 4, 5 and 18 acted quickly upon pea aphids and that compound 5 acted quickly upon corn earworms.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3-10%w of stabilizer(s) and/or other additives such as penetrants or stickers. Dusts are usually formulated as a dust concentrate having a similar composition to that of a wettable powder but without a dispersant, and are diluted in the filed with further solid carrier to give a composition usually containing ½-10%w of toxicant. Granules may be manufactured by agglomeration or impregnation techniques. Generally, granules will contain ½-25%w toxicant and 0-10%w of additives such as stabilizers, slow release modifiers and binding agents. Emulsifiable concentrates usually contain, in addition to the solvent, and when necessary, co-solvent, 10-50%w/v toxicant, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w toxicant, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim:

1. A compound of the formula 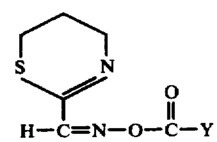 wherein Y is alkyl or alkoxy of from 1 to 20 carbon atoms; alkenyl, alkenyloxy or alkynyl of from 3 to 20 carbon atoms; cycloalkyl, alkylcycloalkyl or cycloalkylalkyl of from 3 to 10 carbon atoms, with from 3 to 6 carbon atoms in the ring; alkoxycarbonylalkyl of from 3 to 10 carbon atoms; alkylthioalkyl of from 2 to 10 carbon atoms; di($C_1$-$C_4$ alkoxy)phosphinyloxy($C_2$-$C_6$ alkenyl)-; styryl; mono($C_1$-$C_4$ alkyl or alkoxy)phenyl; phenyl optionally substituted by from 1 to 3 of one or more of halogen, amino, mono- or di($C_1$-$C_4$alkyl)amino, nitro, cyano or phenoxy, heteroaryl selected from 2-furanyl, 2-thienyl, 2- and 3-pyridyl, and their corresponding phenylmethyl and heteroarylmethyl counterparts; or is wherein *n* is 0, 1, 2, 3 or 4.

* * * * *